United States Patent [19]

Rosi

[11] 4,412,068

[45] Oct. 25, 1983

[54] NOVEL COMPOUNDS OF THE GENTAMICIN CLASS

[75] Inventor: David Rosi, East Greenbush, N.Y.

[73] Assignee: Sterling Drug Inc., New York, N.Y.

[21] Appl. No.: 271,552

[22] Filed: Jun. 8, 1981

[51] Int. Cl.$^3$ .................. C07G 11/00; C12R 1/31; C07H 15/26
[52] U.S. Cl. .................................. 536/13.6; 435/869
[58] Field of Search .................. 564/461; 435/863, 80, 435/172, 869; 536/13.6

[56] References Cited

U.S. PATENT DOCUMENTS

| | | | |
|---|---|---|---|
| 3,091,572 | 5/1963 | Luedemann et al. | 435/863 |
| 3,136,704 | 6/1964 | Charney | 435/863 |
| 3,972,930 | 8/1976 | Daum . | |
| 3,982,996 | 9/1976 | Daum . | |
| 3,984,395 | 10/1976 | Daniels et al. | 435/863 |
| 4,044,123 | 8/1977 | Daniels et al. | 536/13.6 X |
| 4,049,498 | 9/1977 | Weinstein et al. | 435/80 |
| 4,117,221 | 9/1978 | Daniels . | |
| 4,279,997 | 7/1981 | Oka et al. | 435/80 |

FOREIGN PATENT DOCUMENTS 54-58312  5/1979  Japan .

*Primary Examiner*—Delbert R. Gantz
*Assistant Examiner*—Raymond Covington
*Attorney, Agent, or Firm*—William G. Webb; B. Woodrow Wyatt

[57] ABSTRACT

5-Deoxygentamicin $C_{2b}$ and 6'-N-methyl-2-hydroxy- and 6'-N-methyl-5-deoxygentamicins $C_{2b}$ are prepared, as the major fermentation products, by culturing a nutrient medium containing carbohydrates, a source of assimilable nitrogen, essential salts and either D-streptamine or 2,5-dideoxystreptamine with a mutant of *Micromonospora purpurea* and isolating the fermentation products from the nutrient medium. The fermentation products are acylated with an ester of an $\omega$-[N-(benzyloxycarbonyl)amino]-$\alpha$-hydroxy-lower-alkanoic acid after first blocking the primary amino group at the 2'-position with an amine-protecting group, followed by catalytic hydrogenolysis of the benzyloxycarbonyl group and removal of the amine-protecting group to prepare the 1-($\omega$-amino-$\alpha$-hydroxy-lower-alkanoyl) derivatives.

5 Claims, No Drawings

NOVEL COMPOUNDS OF THE GENTAMICIN CLASS

BACKGROUND OF THE INVENTION

1. Field of the Invention

This invention relates to aminocyclitol antibiotics of the gentamicin class, which are useful as antibacterial agents.

2. Description of the Prior Art

Daum et al. U.S. Pat. No. 3,972,930, issued Aug. 3, 1976, disclose 2-hydroxygentamicins $C_1$, $C_2$ and $C_{1a}$ and 5-deoxygentamicins $C_1$, $C_2$ and $C_{1a}$, which are prepared in a fermentative process involving the incorporation, respectively, of D-streptamine and 2,5-dideoxystreptamine into the products using a particular mutant of *Micromonospora purpurea*, namely *M. purpurea* ATCC 31,119, and Daum et al. U.S. Pat. No. 3,982,996, issued Sept. 28, 1976, disclose the fermentative process for the preparation of the same 2-hydroxy- and 2,5-dideoxystreptamine components involving the incorporation either of an appropriate aminocyclitol, e.g. D-streptamine or 2,5-dideoxystreptamine, or certain non-nitrogen containing cyclitols, e.g. scyllo-inosose, scyllo-inosose pentaacetate or 2,4,5-trihydroxycyclohexanone (2,4-cis), using a further mutant of *M. purpurea* ATCC 31,119, namely *M. purpurea* ATCC 31,164. However these patent disclosures do not describe the preparation of 5-deoxygentamicin $C_{2b}$ or 6'-N-methyl-2-hydroxy- or 6'-N-methyl-5-deoxygentamicins $C_{2b}$, which are disclosed and claimed herein, and moreover the presently claimed compounds have not been isolated from, or detected in, the fermentation products obtained by the Daum et al. procedures disclosed in the two above-mentioned patents.

In fact the novel antibiotics of the present invention are produced by a different mutant of *Micromonospora purpurea* which, like *M. purpurea* ATCC 31,119 and *M. purpurea* ATCC 31,164, also incorporates D-streptamine and 2,5-dideoxystreptamine, but which surprisingly produces, so far as is known, none of the "major" components of 2-hydroxygentamicin and 5-deoxygentamicin, i.e. 2-hydroxygentamicins $C_1$ and $C_2$ and 5-deoxygentamicins $C_1$ and $C_2$ produced by the previous mutants, *M. purpurea* ATCC 31,119 and *M. purpurea* ATCC 31,164, but rather produces only 2-hydroxygentamicin $C_{2b}$ from D-streptamine and 5-deoxygentamicin $C_{2b}$ from 2,5-dideoxystreptamine as the major product in each case and lesser amounts of a second component, namely 6'-N-methyl-2-hydroxygentamicin $C_{2b}$ and 6'-N-methyl-5-deoxygentamicin $C_{2b}$.

German Patent Application No. 2,821,948, published Dec. 7, 1978, discloses antibiotic XK-62-2, i.e. gentamicin $C_{2b}$, O-[3-deoxy-4-C-methyl-3-methylamino-β-L-arabinopyranosyl-(1→6)]-O-[2-amino-6-methylamino-2,3,4,6-tetradeoxy-α-D-erythro-hexopyranosyl-(1→4)]-D-2-deoxystreptamine and antibiotic XK-62-4, O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-D-2-deoxystreptamine.

Daniels U.S. Pat. No. 4,117,221, issued Sept. 26, 1978, discloses certain 1-(ω-amino-α-hydroxy-loweralkanoyl) derivatives of gentamicins $C_1$ and $B_1$.

SUMMARY OF THE INVENTION

In a composition of matter aspect, this invention relates to particular 2-hydroxy- and 5-deoxygentamicins, specifically O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-D-streptamine; O-[3-deoxy-4-C-methyl-3-methylamino-β-L-arabinopyranosyl-(1→6)]-O-[2-amino-6-methylamino-2,3,4,6-tetradeoxy-α-D-erythro-hexopyranosyl-(1→4)]-2,5-dideoxystreptamine; and O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-2,5-dideoxystreptamine, which, for the sake of brevity, are designated herein as 6'-N-methyl-2-hydroxygentamicin $C_{2b}$; 5-deoxygentamicin $C_{2b}$; and 6'-N-methyl-5-deoxygentamicin $C_{2b}$, respectively, and to 1-(ω-amino-α-hydroxy-lower-alkanoyl) derivatives thereof.

In a process aspect, the invention relates to a process for preparing the said 5-deoxygentamicin $C_{2b}$ and 6'-N-methyl-2-hydroxy- and 6'-N-methyl-5-deoxygentamicins $C_{2b}$ as fermentation products which comprises culturing a nutrient medium containing carbohydrates, a source of assimilable nitrogen, essential salts and either D-streptamine or 2,5-dideoxystreptamine with *M. purpurea* ATCC 31,849 and isolating said fermentation products.

In a second process aspect, the invention relates to a process for preparing the 1-(ω-amino-α-hydroxylower-alkanoyl) derivatives of 5-deoxygentamicin $C_{2b}$ and 6'-N-methyl-2-hydroxy- and 6'-N-methyl-5-deoxygentamicins $C_{2b}$ which comprises reacting the latter with an acylating agent in order to derivative the primary amine group at the 2'-position with an amine-protecting group; reacting the product with an N-hydroxysuccinimide ester of an ω-[N-(benzyloxycarbonyl)amino]-α-hydroxylower-alkanoic acid; subjecting the product to catalytic reduction to effect hydrogenolysis of the benzyloxycarbonyl group in the resulting product; and hydrolysis of the 2'-amino-protecting group.

DETAILED DESCRIPTION INCLUSIVE OF THE PREFERRED EMBODIMENTS

More specifically, this invention relates to compounds having the formula

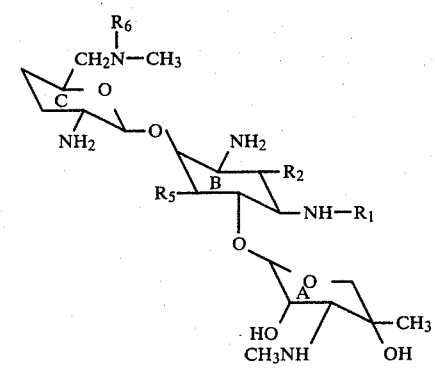

where $R_1$ is hydrogen or an ω-amino-α-hydroxy-lower-alkanoyl group having the formula

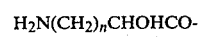

where n is one of the integers 1 or 2; $R_2$ and $R_5$ are either both hydroxy or both hydrogen; and $R_6$ is hydrogen or methyl, $R_2$ being hydroxy only when $R_6$ is methyl, the letters A, B and C being used to identify, for later reference purposes herein, the β-L-arabinopyranosyl, the streptamine (or 2,5-dideoxystreptamine) and the α-D-erythro-hexopyranosyl moieties, respectively.

The compounds of the invention embraced by formula I above, where $R_1$ in each case is hydrogen, are designated Compounds 1, 2, and 3 as follows:

Compound 1: $R_2$ and $R_5$ are hydroxy; $R_6$ is methyl;
Compound 2: $R_2$, $R_5$ and $R_6$ are hydrogen;
Compound 3: $R_2$ and $R_5$ are hydrogen; $R_6$ is methyl, these compounds being chemically designated as O-[3-deoxy-4-C-methyl-3-methylamino-β-L-arabinopyranosyl-(1→6)]-O-[2-amino-6-dimethylamino-2,3,4,6-tetradeoxy-α-D-erythrohexopyranosyl-(1→4)]-D-streptamine (Compound 1); O-[3-deoxy-4-C-methyl-3-methylamino-β-L-arabinopyranosyl-(1→6)]-O-[2-amino-6-methylamino-2,3,4,6-tetradeoxy-α-D-erythrohexopyranosyl-(1→4)]-2,5-dideoxystreptamine (Compound 2); and O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-2,5-dideoxystreptamine (Compound 3), respectively.

The compounds of formula I where $R_1$ is hydrogen are prepared by the method described in Shier et al. U.S. Pat. No. 3,669,838 which comprises culturing a nutrient medium containing carbohydrates, a source of assimilable nitrogen, essential salts and D-streptamine with a mutant of *Micromonospora purpurea*, namely *M. purpurea* ATCC 31,849. The latter is itself a mutant of *M. purpurea* ATCC 31,848, which in turn is a mutant of *M. purpurea* NRRL 2953. In accordance with the procedure described by Shier et al., the nature of mutant *M. purpurea* ATCC 31,849 is such that, unlike *M. purpurea* NRRL 2953 and *M. purpurea* ATCC 31,848 from which it is derived, *M. purpurea* ATCC 31,849 is not capable of synthesizing the aminocyclitol moiety of the antibiotic from a nutrient medium but is capable of incorporating aminocyclitols, such as D-streptamine or 2,5-dideoxystreptamine, into an antibiotic when either of the latter is added to the nutrient medium. *M. purpurea* ATCC 31,849 is thus an idiotroph requiring an exogenous source of an aminocyclitol to produce antibiotics. On the other hand, *M. purpurea* NRRL 2953 and *M. purpurea* ATCC 31,848 are both prototrophs and can only synthesize gentamicin components from a nutrient medium.

*M. purpurea* ATCC 31,849 is, however, further distinguished from other known idiotrophs of *M. purpurea*, such as *M. purpurea* ATCC 31,119 and *M. purpurea* ATCC 31,164, in that *M. purpurea* ATCC 31,849 incorporates D-streptamine or 2,5-dideoxystreptamine to form exclusively the D-streptamine analog of Compound 2 (from D-streptamine) or Compound 2 (from 2,5-dideoxystreptamine), respectively, and lesser amounts of Compounds 1 or 3, respectively, as these compounds are identified above. However, mutant *M. purpurea* ATCC 31,849 is not known to produce any of the usual "major components" of 2-hydroxy- or 5-deoxygentamicin, i.e. 2-hydroxy- or 5-deoxygentamicin $C_1$ and $C_2$ such as produced by *M. purpurea* ATCC 31,119 or *M. purpurea* ATCC 31,164. (See Daum et al. U.S. Pat. Nos. 4,028,188 and 3,982,996.)

The compounds of formula I where $R_1$ represents an ω-amino-α-hydroxy-lower-alkanoyl group are prepared by the method described by Daniels U.S. Pat. No. 4,117,221. This method comprises reacting a compound of formula I, where $R_1$ is hydrogen, with an acylating agent in order to derivatize the primary amine group at the 2'-position with an amine-protecting group, for example the trifluoroacetyl, t-butoxycarbonyl or benzyloxycarbonyl group, followed by reaction of the resulting derivative with an N-hydroxysuccinimide ester having the formula II:

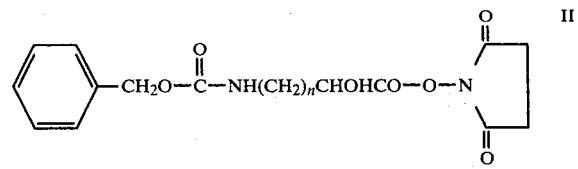

where n has the meanings given above.

In the course of reacting a compound of formula I with an acylating agent, other free primary or secondary amine groups in the molecule, for example the primary amine groups at the 1- and 3-positions of the aminocyclitol moiety (ring B in formula I) and the secondary amine groups at the 3" and 6'-position (in rings A and C, respectively, in formula I) may also react, thus necessitating separation of the reaction products to recover the 2'-acylated material.

The products thus obtained are then subjected to hydrogenolysis with hydrogen over a catalyst in order to effect removal of the benzyloxycarbonyl group, and in a final step, the amine-protecting group is removed by hydrolysis with trifluoroacetic acid.

The 2'-trifluoroacetyl, 2'-t-butoxycarbonyl or 2'-benzyloxycarbonyl derivatives of the compounds of formula I as described above are prepared by reaction of a compound of formula I, where $R_1$ is hydrogen, with, respectively, trifluoroacetic anhydride, t-butyl S-(4,6-dimethylpyrimidin-2-yl) thiolcarbonate or benzyl chloroformate in the presence of a molar excess of an acid acceptor, for example a tri-lower-alkylamine or an alkali metal carbonate, for example sodium or potassium carbonate. The reaction is carried out in an aqueous solution which may optionally be diluted with a water miscible organic solvent, for example tetrahydrofuran, dioxane, dimethylformamide and the like.

The 1-(ω-amino-α-hydroxy-lower-alkanoyl) derivatives of the resulting 2'-amine-blocked compounds are prepared by reaction of the latter with a molar equivalent amount of an N-hydroxysuccinimide ester of formula II, preferably at a temperature from −10° C. to about 10° C., in an aqueous solution of a water miscible organic solvent, for example tetrahydrofuran, dioxane, ethyleneglycol dimethyl ether, dimethylacetamide, dimethylformamide, propyleneglycol dimethyl ether and the like.

Hydrogenolysis of the resulting products is carried out over a palladium-on-charcoal catalyst in an inert, water miscible organic solvent, for example, methanol, ethanol, dioxane, tetrahydrofuran, ethyleneglycol dimethyl ether, propyleneglycol dimethyl ether and the like.

Hydrolysis of the amine-protecting group (i.e. the trifluoroacetyl, benzyloxycarbonyl or the t-butoxycarbonyl group) in the resulting products is carried out by dissolving them in trifluoroacetic acid at ambient temperature. If desired the product can be isolated in the form of the trifluoroacetate salt by dilution of the reaction mixture with diethyl ether, and the salt can, in turn, be converted to the free base form, preferably by passing an aqueous solution of the salt form over a basic ion exchange resin in the hydroxide ion form and lyophilizing the aqueous solution thus produced.

Due to the presence of basic amine groupings, the free base forms represented by formula I above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, α-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indole acetic acid, barbituric acid, sulfamic acid, methanesulfonic acid, ethanesulfonic acid, isethionic acid, benzenesulfonic acid, 4-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid and the like.

All of the acid-addition salts are useful as sources of the free base forms by reaction of the salts with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically acceptable acids, for example, sulfuric acid, hydrochloric acid, lactic acid, tartaric acid and the like, are of course employed.

The compounds of formula I have been tested in a standard serial dilution antibacterial test and have been found to have antibacterial activity, and are useful as antibacterial agents.

The compounds of formula I are primarily intended for oral, topical or parenteral administration and can be prepared for use by suspension, either in the form of their free bases or as pharmaceutically acceptable non-toxic acid-addition salts, in an inert carrier such as polyethyleneglycol, or by tabletting or encapsulation for oral administration either alone or with suitable adjuvants, or alternatively they can be formulated with conventional creams or jellies for topical application.

The molecular structures of the compounds of the invention were assigned on the basis of their method of preparation; by study of their chromatographic characteristics determined by thin layer chromatographic (tlc) analyses; by their nuclear magnetic resonance (nmr) and mass spectra; by the correspondence between calculated and found values for elementary analyses for the elements; and by study of the chromatographic characteristics and determination of the mass spectra of derivatives of the final products.

The following specific examples are illustrative of the manner of making the compounds of the invention.

EXEMPLARY DISCLOSURE

Example 1

The mutant organism, M. purpurea ATCC 31,848 was obtained from M. purpurea NRRL 2953, and M. purpurea ATCC 31,849 was, in turn, obtained from the former, in both cases, using the mutation procedures described in U.S. Pat. No. 3,972,930. The mutants were maintained on N-Z amine agar slants in Medium 1 constituted in distilled water as follows:

|  | g./l. |
| --- | --- |
| Glucose | 10 g. |
| Soluble starch | 20 g. |
| Difco yeast extract | 5 g. |
| N—Z—Amine-Type A (Difco) | 5 g. |
| CaCO$_3$ | 1 g. |
| Agar | 15 g. |

A first stage seed of M. purpurea ATCC 31,849 was prepared by inoculating a loopful from the slant to 50 ml. of a germination medium (Medium 2) in a 250 ml. flask constituted in distilled water as follows:

| Beef extract | 0.3% |
| --- | --- |
| Tryptone | 0.5% |
| Dextrose | 0.1% |
| Soluble starch | 2.4% |
| Yeast extract | 0.5% |
| CaCO$_3$ | 0.4% |

A 5% inoculum from this tank stage seed was used to inoculate six 10 liter fermentations using production Medium 3 constituted in distilled water as follows:

| Glucose | 2% |
| --- | --- |
| Soy bean meal | 0.75% |
| Amberflave (Amber Labs) | 0.75% |
| CaCO$_3$ | 0.4% |
| CoCl$_2$.6H$_2$O | 0.0001% |
| Antifoam | 0.01% |

300 micrograms per ml. of D-streptamine being added as substrate to three tanks and 600 micrograms per ml. being added to the other three. Fermentation was carried out for one hundred forty hours at 28°–29° C., and the tanks were sparged with filtered air at five liters/minute. The fermentations were then combined, the pH was adjusted to 2.0 with concentrated sulfuric acid, and the mixture allowed to cool and filtered with filter aid.

The filtrate was adjusted to pH 7.0 with 10 N sodium hydroxide and filtered through filter paper to remove a flocculant precipitate. The clear filtrate was then passed over four liters of a column of BioRex 70 ion exchange resin (ammonium form). The column was washed first with twenty liters of water, and antibiotic material was then eluted first with 0.02 N ammonium hydroxide (4 liters), then with four liters of 0.2 N ammonium hydroxide and finally with 8 liters of 2.0 N ammonium hydroxide, the presence of antibiotic activity in the eluates being followed by disc diffusion assay against *B. subtilis* as challenge organism. The first 7 liters of eluate displayed little or no antibiotic activity and were discarded. The next 5 liters of eluate were combined and concentrated in vacuo to a volume of 250 ml. The pH of the concentrate was adjusted to 5.5 with 6 N sulfuric acid and cooled for about seventy-two hours. The solid which had separated from the cooled solution was filtered off, and the filtrate (250 ml.) was added dropwise to 2.5 liters of methanol with stirring. The solid which separated was again collected, redissolved in 200 ml. of water and the solution filtered again. The methanol precipitation process on the filtrate was repeated twice more as described above, and the final solids were dissolved in 75 ml. of water. Repeated extraction of the latter with the lower phase of a 2:1:1 mixture of chloroform:isopropyl alcohol:concentrated ammonium hydroxide and evaporation of the combined extracts to dryness afforded an amber colored residue weighing 1.98 g. (base). This was dissolved in 25 ml. of water, the pH of the solution was adjusted to pH 5.5 with 6 N sulfuric acid, the solution was filtered through filter aid, and the filtrate was added dropwise to 300 ml. of methanol with stirring. The solid which separated was collected, washed with acetone and dried to give 2.437 g. of crude product as the sulfate salt. A second fermentation carried out as described above yielded 2.03 g. of crude product as base.

About 1.5 g. of the former was dissolved in about 1.8 ml. of water and the solution applied as narrow bands to nine 20×40 cm. silica gel thin layer chromatographic plates. The plates were developed using the lower phase of a 1:1:1 mixture of chloroform:methanol:concentrated ammonium hydroxide, and components were located using ninhydrin spray on a small portion of the plates. The components were separated by scraping from the plate and eluting them from the adsorbent with the same developing solvent. The extracts were combined and concentrated in vacuo. The less polar component ($R_f=0.33$) was set aside for further work, as described below, the more polar component ($R_f=0.27$) was combined with 0.29 g. of similar material from another run, and the combined sample was dissolved in 10 ml. of water. The solution was acidified to pH 4.2 with sulfuric acid, the resulting solution was extracted first with 50 ml. of chloroform to remove a yellow coloration, and the raffinate was then exhaustively extracted with the lower phase of a 2:1:1 mixture of chloroform:isopropyl alcohol:concentrated ammonium hydroxide. The extracts were combined, filtered and taken to dryness in vacuo to give 1.1 g. of a residue which was dissolved in 10 ml. of water. The solution was acidified with 1.0 M sulfuric acid to pH 5.6 (10.9 ml. of acid), charcoaled and filtered, and the filtrate was frozen and lyophilized to give 1.68 g. of O-[3-deoxy-4-C-methyl-3-methylamino-β-L-arabinopyranosyl-(1→6)]-O-[2-amino-6-methylamino-2,3,4,6-tetradeoxy-α-D-erythro-hexopyranosyl-(1→4)]-D-streptamine.2.3 $H_2SO_4$.2 $H_2O$, m.p. 250°–251° C.

Anal. Calcd for $C_{20}H_{41}N_5O_8.2.3H_2SO_4.2H_2O$: C, 32.42; H, 6.73; N, 9.45; S, 9.95; Found: C, 32.32; H, 6.87; N, 9.29; S, 9.84.

The nmr spectrum of the latter against an external trimethylsilane standard showed the presence of two N-$CH_3$ groups [δ(ppm)=3.46, 3.28] and one C-$CH_3$ group [δ(ppm)=1.90].

The mass spectrum of the compound showed mass peaks at M/e+479, 160 (A ring sugar) and 143 (C ring sugar).

The 2.03 g. sample of crude base described above was dissolved in water and developed on twenty-one 20×40 cm. silica gel tlc plates as described above using the lower phase of a 1:1:1 mixture of chloroform:methanol:concentrated ammonium hydroxide as developing solvent. There was thus obtained 1.46 g. of less polar material ($R_f=0.33$) previously obtained. The combined sample was dissolved in 20 ml. of water and the pH adjusted to 5.5 by the addition of 5.5 ml. of 1 N sulfuric acid. The resulting solution was extracted once with chloroform, then charcoaled, filtered, concentrated to a volume of about 20 ml. in vacuo and lyophilized. The resulting solid (1.07 g.) was dried in a vacuum oven to give 1.0 g. of O-[3-deoxy-4-C-methyl-3-methylamino-β-L-arabinopyranosyl-(1→6)]-O-[2-amino-6-dimethylamino-2,3,4,6-tetradeoxy-α-D-erythrohexopyranosyl-(1→4)]-D-streptamine sulfate (4:7) hydrate(2:9), m.p. 244°–246° C.

Anal. Calcd for $C_{21}H_{43}N_6O_8.1.75H_2SO_4.4.5H_2O$: C, 33.80; H, 7.50; N, 9.38; S, 7.52. Found: C, 33.84; H, 7.26; N, 9.66; S, 7.39.

The nmr spectrum of the latter against an external trimethylsilane standard showed the presence of three N-$CH_3$ groups [δ(ppm)=3.28] and one C-$CH_3$ group [δ(ppm)=1.83].

The mass spectrum of the compound showed mass peaks at M/e+ 493, 160 (A ring sugar) and 157 (C ring sugar).

The presence of a single acylatable amino function in the C ring sugar of the latter was demonstrated by the following procedure: A solution of 5 mg. of the compound in a solution of 0.2 ml. of pyridine containing a few drops of acetic anhydride was heated under reflux for four hours and the mixture taken to dryness in vacuo to give material having $R_f=0.70$ on thin layer chromatography on silica gel plates using the lower phase of 1:1:1 chloroform:methanol:concentrated ammonium hydroxide. The mass spectrum of the product showed mass peaks at M/e+ 788 (seven acetyl groups), 244 (A ring plus two acetyl groups) and 199 (C ring plus one acetyl group).

Example 2

Following a procedure similar to that described in Example 1 above, 100 μg./ml. of 2,5-dideoxystreptamine were added to each of nine 10 liter fermentations in production Medium 3 along with *M. purpurea* ATCC 31,849, and the fermentations were carried out at 28°–29° C. for one hundred and forty hours while sparging with air at five liters/minute. The fermentations were then combined and worked up as before, antibiotically active material being obtained by elution from a BioRex 70 ion exchange resin column (ammonium form). The column was first eluted with 2 liters of 0.02 N ammonium hydroxide which was discarded. Further elution with 10 liters of 0.02 N ammonium hydroxide afforded the antibiotic which was isolated as described above. Repeated methanol precipitations of the product as described in Example 1 followed by extraction with the lower phase of a 2:1:1 chloroform:isopropyl alcohol:concentrated ammonium hydroxide mixture and conversion to the sulfate salt gave 1.4 g. of crude product. An additional 2.6 g. of product was obtained from two similar runs. The combined sample was purified by thin layer chromatography on a total of thirty-four 20×40 cm. chromatography plates and developed with the lower phase of a 1:1:1 mixture of chloroform:methanol:concentrated ammonium hydroxide using ninhydrin to locate the components. The components so separated were scraped off the plates and eluted from the adsorbent with the same developing solvent. The major component ($R_f$=0.35) weighing 88 mg. was dissolved in chloroform/methanol, the solution filtered through filter aid and the filtrate evaporated to dryness to give 76.7 mg. of O-[3-deoxy-4-C-methyl-3-methylamino-β-L-arabinopyranosyl-(1→6)]-O-[2-amino-6-methylamino-2,3,4,6-tetradeoxy-α-D-erythrohexopyranosyl-(1→4)]-2,5-dideoxystreptamine.

The nmr spectrum of the latter against trimethylsilane as external standard gave chemical shifts as follows: 5.55, 5.44 ppm (2 O-CH-O); 5.23 ppm (10 NH, OH); 2.7–4.6 ppm (4 CHN, 1 CH$_2$N, 4 CHO, 1 CH$_2$-O); 2.97; 3.02 ppm (2 N-CH$_3$); 1.72 (1 CH$_3$C); 1.4–2.7 ppm (4 CH$_2$C).

The mass spectrum of the compound showed mass peaks at M/e$^+$ 447, 160 (A ring sugar) and 143 (C ring sugar).

The minor component ($R_f$=0.41) was similarly isolated from tlc plates to give material whose mass spectrum showed peaks at MH$^+$ 462, 160 (A ring sugar) and 157 (C ring sugar), consistent with O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-2,5-dideoxystreptamine.

Example 3

It is contemplated that, by the dropwise addition of a solution of t-butyl S-(4,6-dimethylpyrimidin-2-yl) thiolcarbonate in dioxane to a solution containing a molar equivalent amount of O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-D-streptamine in water containing a molar excess of triethylamine, there can be obtained O-[3-deoxy-4-C-methyl-3-methylamino-β-L-arabinopyranosyl-(1→6)]-O-[2-(t-butoxycarbonyl)amino-6-dimethylamino-2,3,4,6-tetradeoxy-α-D-erythro-hexopyranosyl-(1→4)]-D-streptamine which, on dissolving in aqueous methanol and treatment at 5° C. with stirring with a molar equivalent amount of the N-hydroxysuccinimide ester of S-(−)-δ-(benzyloxycarbonyl)amino-α-hydroxybutyric acid in dimethylformamide, will afford 1-[S-(−)-δ-(benzyloxycarbonyl)-amino-α-hydroxybutyryl]-O-[3-deoxy-4-C-methyl-3-methylamino-β-L-arabinopyranosyl-(1→6)]-O-[2-(t-butoxycarbonyl)amino-6-dimethylamino-2,3,4,6-tetradeoxy-α-D-erythro-hexopyranosyl-(1→4)]-D-streptamine which, on catalytic reduction with hydrogen over 10% palladium-on-charcoal at a pressure of 50 pounds p.s.i.g., will afford 1-[S-(−)-δ-amino-α-hydroxybutyryl]-O-[3-deoxy-4-C-methyl-3-methylamino-β-L-arabinopyranosyl-(1→6)]-O-[2-(t-butoxycarbonyl)amino-6-dimethylamino-2,3,4,6-tetradeoxy-α-D-erythro-hexaopyranosyl-(1→4)]-D-streptamine which, on dissolving in trifluoroacetic acid, allowing the solution to stand at ambient temperature for five minutes and isolating the product from a neutral medium, will afford 1-[S-(−)-γ-amino-α-hydroxybutyryl]-O-[3-deoxy-4-C-methyl-3-methylamino-β-L-arabinopyranosyl-(1→6)]-O-[2-amino-6-dimethylamino-2,3,4,6-tetradeoxy-α-D-erythrohexopyranosyl-(1→4)]-D-streptamine.

Example 4

It is contemplated that, by the dropwise addition of a solution of t-butyl S-(4,6-dimethylpyrimidin-2-yl) thiolcarbonate in dioxane to a solution containing a molar equivalent amount of O-[3-deoxy-4-C-methyl-3-methylamino-β-L-arabinopyranosyl-(1→6)]-O-[2-amino-6-methylamino-2,3,4,6-tetradeoxy-α-D-erythro-hexopyranosyl-(1→4)]-2,5-dideoxystreptamine in water containing a molar excess of triethylamine, there can be obtained O-[3-deoxy-4-C-methyl-3-methylamino-β-L-arabinopyranosyl-(1→6)]-O-[2-(t-butoxycarbonyl)amino-6-methylamino-2,3,4,6-tetradeoxy-α-D-erythro-hexopyranosyl-(1→4)]-2,5-dideoxystreptamine which, on dissolving in aqueous methanol and treatment at 5° C. with stirring with a molar equivalent amount of the N-hydroxysuccinimide ester of S-(−)-γ-(benzyloxycarbonyl)amino-α-hydroxybutyric acid in dimethylformamide, will afford 1-[S-(−)-γ-(benzyloxycarbonyl)amino-α-hydroxybutyryl]-O-[3-deoxy-4-C-methyl-3-methylamino-β-L-arabinopyranosyl-(1→6)]-O-[2-(t-butoxycarbonyl)amino-6-methylamino-2,3,4,6-tetradeoxy-α-D-erythro-hexopyranosyl-(1→4)]-2,5-dideoxystreptamine which, on catalytic reduction with hydrogen over 10% palladium-on-charcoal at a pressure of 50 pounds p.s.i.g., will afford 1-[S-(−)-γ-amino-α-hydroxybutyryl]-O-[3-deoxy-4-C-methyl-3-methylamino-β-L-arabinopyranosyl-(1→6)]-O-[2-(t-butoxycarbonyl)amino-6-methylamino-2,3,4,6-tetradeoxy-α-D-erythro-hexopyranosyl-(1→4)]-2,5-dideoxystreptamine which, on dissolving in trifluoroacetic acid, allowing the solution to stand at ambient temperature for five minutes and isolating the product from a neutral medium, will afford 1-[S-(−)-γ-amino-α-hydroxybutyryl]-O-[3-deoxy-4-C-methyl-3-methylamino-β-L-arabinopyranosyl-(1→6)]-O-[2-amino-6-methylamino-2,3,4,6-tetradeoxy-α-D-erythro-hexopyranosyl-(1→4)]-2,5-dideoxystreptamine.

Example 5

It is contemplated that, by the dropwise addition of a solution of t-butyl S-(4,6-dimethylpyrimidin-2-yl) thiolcarbonate in dioxane to a solution containing a molar equivalent amount of O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-2,5-dideoxystreptamine in water containing a molar excess of triethylamine, there can be obtained O-[3-deoxy-4-C-methyl-3-methylamino-β-L-arabinopyranosyl-(1→6)]-O-[2-(t-butoxycarbonyl)amino-6-dimethylamino-2,3,4,6-tetradeoxy-α-D-erythro-hexopyranosyl-(1→4)]-2,5-dideoxystreptamine which, on dissolving in aqueous methanol and treatment at 5° C. with stirring with a molar equivalent amount of the N-hydroxysuccinimide ester of S-(−)-γ-benzyloxycarbonyl)amino-α-hydroxybutyric acid in dimethylformamide, will afford 1-[S-(−)-γ-(benzyloxycarbonyl)amino-α-hydroxybutyryl]-O-[3-deoxy-4-C-methyl-3-methylamino-β-L-arabinopyranosyl-(1→6)]-O-[2-(t-butoxycarbonyl)amino-6-dimethylamino-2,3,4,6-tetradeoxy-α-D-erythro-hexopyranosyl-(1→4)]-2,5-dideoxystreptamine which, on catalytic reduction with hydrogen over a 10% palladium-on-charcoal at a pressure of 50 pounds p.s.i.g., will afford 1-[S-(−)-γ-amino-α-hydroxybutyryl]-O-[3-deoxy-4-C-methyl-3-methylamino-β-L-arabinopyranosyl-(1→6)]-O-[2-(t-butoxycarbonyl)amino-6-dimethylamino-2,3,4,6-tetradeoxy-α-D-erythrohexopyranosyl-(1→4)]-2,5-dideoxystreptamine which, on dissolving in trifluoroacetic acid, allowing the solution to stand at ambient temperature for five minutes and isolating the product from a neutral medium, will afford 1-[S-(−)-γ-amino-α-hydroxybutyryl]-O-[3-deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-2,5-dideoxystreptamine.

BIOLOGICAL TEST RESULTS

The useful antibacterial activity of the compounds of the invention was demonstrated by in vitro antibacterial activity tests against a variety of microorganisms using a standard serial dilution method. The results, expressed in terms of the minimum inhibitory concentration (MIC γ/ml.), are given in the table below. For comparative purposes, corresponding data are given for hydroxygentamican (HOGM), gentamicin (GM) and hydroxygentamicin $C_{2b}$ (HOGM $C_{2b}$).

| Microorganism | Cpd. 1 | HOGM | GM | HOGM $C_{2b}$ |
|---|---|---|---|---|
| S. aureus Smith | 3.9 | 1.0 | 0.5 | 1.0 |
| S. aureus Giorgio | 15.6 | 3.9 | 1.0 | 3.9 |
| E. coli JR 89 | 250 | 31.3 | 31.3 | 125 |
| E. coli JR 76.2 | 31.3 | 7.8 | 125 | 7.8 |
| E. coli Vogel | 3.9 | 1.95 | 1.95 | 1.95 |
| E. coli W677/HJR66 | 250 | 62.5 | >500 | 62.5 |
| Ent. cloacae A-20960 | 3.9 | 1.95 | 15.6 | 1.95 |
| K. pneumoniae A-20636 | 15.6 | 1.95 | 15.6 | 3.9 |
| K. pneumoniae 39645 | 15.6 | 1.0 | 0.25 | 1.0 |
| Pr. mirabilis MGH-1 | 3.9 | 3.9 | 1.0 | 1.95 |
| Providencia stuartii A-20894 | 500 | 250 | 250 | >500 |
| Ps. aeruginosa A | 15.6 | 1.95 | 0.5 | 1.95 |
| Ps. aeruginosa Capetown 18 | >500 | 31.3 | 31.3 | 125 |
| Ps. aeruginosa MGH-2 | 15.6 | 3.9 | 0.5 | 3.9 |
| Ps. aeruginosa A-20717 | 250 | 31.3 | 7.8 | 62.5 |
| Ps. aeruginosa A-20741 | >500 | >500 | >500 | >500 |
| Ps. aeruginosa A-20897 | 125 | 62.5 | >500 | >500 |
| Ps. aeruginosa 10197-1 | 15.6 | 1.95 | 1.0 | 1.95 |
| Ps. aeruginosa C | * | 3.9 | 1.0 | 3.9 |
| Ps. aeruginosa 7700 | 15.6 | 15.6 | 1.95 | 7.8 |

*Culture did not grow

I claim:
1. A member of the group consisting of (A) a compound having the formula:

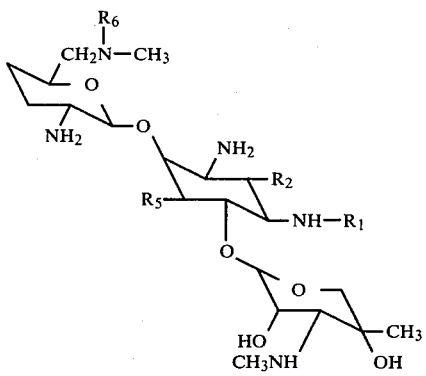

where $R_1$ is hydrogen or the group, $H_2N(CH_2)_n CHOH-CO-$, where n is one of the integers 1 or 2; $R_2$ and $R_5$ are either both hydroxy or both hydrogen; and $R_6$ is hydrogen or methyl, $R_2$ being hydroxy only when $R_6$ is methyl; and (B) acid-addition salts thereof.

2. O-[3-Deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-D-streptamine according to claim 1.

3. O-[3-Deoxy-4-C-methyl-3-methylamino-β-L-arabinopyranosyl-(1→6)]-O-[2-amino-6-methylamino-2,3,4,6-tetradeoxy-α-D-erythro-hexopyranosyl-(1→4)]-2,5-dideoxystreptamine according to claim 1.

4. O-[3-Deoxy-4-C-methyl-3-methylamino-β-L-arabinopyranosyl-(1→6)]-O-[2-amino-6-dimethylamino-2,3,4,6-tetradeoxy-α-D-erythro-hexopyranosyl-(1→4)]-2,5-dideoxystreptamine according to claim 1.

5. A process for preparing a compound having the formula:

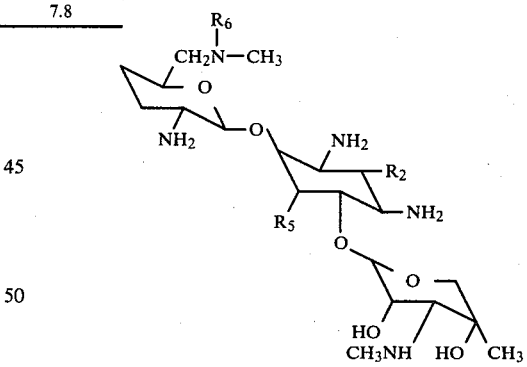

which comprises culturing micromonospora purpurea ATCC 31,849 in a nutrient medium containing carbohydrates, a source of assimilable nitrogen, essential salts and either D-streptamine, to prepare, as a major component, the compound where $R_2$ and $R_5$ are both hydroxy and $R_6$ is hydrogen and, as a minor component, the compound where $R_2$ and $R_5$ are both hydroxy and $R_6$ is methyl, or 2,5-dideoxystreptamine, to prepare, as the major component, the compound where $R_2$, $R_5$ and $R_6$ are each hydrogen and, as a minor component, the compound where $R_2$ and $R_5$ are both hydrogen and $R_6$ is methyl and isolating the said compounds from the nutrient medium.

* * * * *

UNITED STATES PATENT AND TRADEMARK OFFICE
CERTIFICATE OF CORRECTION

PATENT NO.    :   4,412,068
DATED         :   October 25, 1983
INVENTOR(S)   :   David Rosi It is certified that error appears in the above-identified patent and that said Letters Patent is hereby corrected as shown below:

Column 2, line 31, change "derivative" to read - - derivatize - -.

Column 2, line 38, change "amino" to read - - amine - -.

Column 4, line 22, change "position" to read - - positions - -.

Signed and Sealed this

Fifth Day of March 1985

[SEAL]

*Attest:*

DONALD J. QUIGG

*Attesting Officer*    *Acting Commissioner of Patents and Trademarks*